(12) United States Patent
Podhajsky

(10) Patent No.: US 7,749,217 B2
(45) Date of Patent: Jul. 6, 2010

(54) METHOD AND SYSTEM FOR OPTICALLY DETECTING BLOOD AND CONTROLLING A GENERATOR DURING ELECTROSURGERY

(75) Inventor: Ronald J. Podhajsky, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 808 days.

(21) Appl. No.: 10/513,764

(22) PCT Filed: May 6, 2003

(86) PCT No.: PCT/US03/14155

§ 371 (c)(1),
(2), (4) Date: Jul. 5, 2005

(87) PCT Pub. No.: WO03/092520

PCT Pub. Date: Nov. 13, 2003

(65) Prior Publication Data

US 2006/0025760 A1    Feb. 2, 2006

Related U.S. Application Data

(60) Provisional application No. 60/378,290, filed on May 6, 2002.

(51) Int. Cl.
*A61B 18/18* (2006.01)
*A61B 6/00* (2006.01)
(52) U.S. Cl. ............................. 606/34; 606/41; 600/477
(58) Field of Classification Search ............ 606/32–34, 606/40–42, 45–52, 7–15; 600/473–480
See application file for complete search history.

(56) References Cited

U.S. PATENT DOCUMENTS

| | | | |
|---|---|---|---|
| 1,787,709 | A | 1/1931 | Wappler |
| 1,813,902 | A | 7/1931 | Bovie |
| 1,841,968 | A | 1/1932 | Lowry |
| 1,863,118 | A | 6/1932 | Liebel |
| 1,945,667 | A | 2/1934 | Rawls |
| 2,827,056 | A | 3/1958 | Degelman |
| 2,849,611 | A | 8/1958 | Adams |

(Continued)

FOREIGN PATENT DOCUMENTS

DE    179607    3/1905

(Continued)

OTHER PUBLICATIONS

International Search Report EP06022028.2 dated Feb. 5, 2007.

(Continued)

*Primary Examiner*—Michael Peffley

(57) ABSTRACT

A method and electrosurgical system for optically detecting blood and controlling an electrosurgical generator are provided. An optical blood detection system is used for optically detecting blood and may be included as an integral part of the overall electrosurgical system's circuitry, or may be designed as a separate unit that connects to, and controls, an electrosurgical generator. The optical blood detection system may be embodied through a variety of analog, digital and/or optical circuit components or arrangements, including software running on computational and memory circuitry. The optical blood detection system controls the output mode and energy of the electrosurgical generator in accordance with the amount of blood detected.

20 Claims, 6 Drawing Sheets

U.S. PATENT DOCUMENTS

| | | |
|---|---|---|
| 2,982,881 A | 5/1961 | Reich |
| 3,058,470 A | 10/1962 | Seeliger et al. |
| 3,089,496 A | 5/1963 | Degelman |
| 3,163,165 A | 12/1964 | Islikawa |
| 3,252,052 A | 5/1966 | Nash |
| 3,391,351 A | 7/1968 | Trent |
| 3,402,326 A | 9/1968 | Guasco et al. |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,604 A | 9/1978 | Shaw et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,237,891 A | 12/1980 | DuBose et al. |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,586,120 A | 4/1986 | Malik et al. |
| 4,590,934 A | 5/1986 | Malis et al. |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,646,222 A | 2/1987 | Okado et al. |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |

| | | | | | | |
|---|---|---|---|---|---|---|
| 4,691,703 A | 9/1987 | Auth et al. | | 5,334,193 A | 8/1994 | Nardella |
| 4,712,559 A | 12/1987 | Turner | | 5,341,807 A | 8/1994 | Nardella |
| 4,727,874 A | 3/1988 | Bowers et al. | | 5,342,356 A | 8/1994 | Ellman |
| 4,735,204 A | 4/1988 | Sussman et al. | | 5,342,357 A | 8/1994 | Nardella |
| 4,739,759 A | 4/1988 | Rexroth et al. | | 5,342,409 A | 8/1994 | Mullett |
| 4,741,334 A | 5/1988 | Irnich | | 5,348,554 A | 9/1994 | Imran et al. |
| 4,754,757 A | 7/1988 | Feucht | | 5,370,645 A | 12/1994 | Klicek et al. |
| 4,788,634 A | 11/1988 | Schlecht et al. | | 5,370,672 A | 12/1994 | Fowler et al. |
| 4,805,621 A | 2/1989 | Heinze et al. | | 5,370,675 A | 12/1994 | Edwards et al. |
| 4,818,954 A | 4/1989 | Flachenecker et al. | | 5,372,596 A | 12/1994 | Klicek et al. |
| 4,827,911 A | 5/1989 | Broadwin et al. | | 5,383,874 A | 1/1995 | Jackson |
| 4,827,927 A | 5/1989 | Newton | | 5,383,876 A | 1/1995 | Nardella |
| 4,832,024 A | 5/1989 | Boussignac et al. | | 5,383,917 A | 1/1995 | Desai et al. |
| 4,848,335 A | 7/1989 | Manes | | 5,385,148 A | 1/1995 | Lesh et al. |
| 4,848,355 A | 7/1989 | Nakamura et al. | | 5,396,062 A | 3/1995 | Eisentraut et al. |
| 4,860,745 A | 8/1989 | Farin et al. | | 5,400,267 A | 3/1995 | Denen et al. |
| 4,862,889 A | 9/1989 | Feucht | | 5,403,311 A | 4/1995 | Abele et al. |
| 4,880,719 A | 11/1989 | Murofushi et al. | | 5,403,312 A | 4/1995 | Yates et al. |
| 4,887,199 A | 12/1989 | Whittle | | 5,409,000 A | 4/1995 | Imran |
| 4,890,610 A | 1/1990 | Kirwan et al. | | 5,409,006 A | 4/1995 | Buchholtz et al. |
| 4,903,696 A | 2/1990 | Stasz et al. | | 5,409,485 A | 4/1995 | Suda |
| 4,907,589 A | 3/1990 | Cosman | | 5,413,573 A | 5/1995 | Koivukangas |
| 4,922,210 A | 5/1990 | Flachenecker et al. | | 5,414,238 A | 5/1995 | Steigerwald et al. |
| 4,931,047 A | 6/1990 | Broadwin et al. | | 5,417,719 A | 5/1995 | Hull et al. |
| 4,931,717 A | 6/1990 | Gray et al. | | 5,422,567 A | 6/1995 | Matsunaga |
| 4,938,761 A | 7/1990 | Ensslin | | 5,423,808 A | 6/1995 | Edwards et al. |
| 4,942,313 A | 7/1990 | Kinzel | | 5,423,809 A | 6/1995 | Klicek |
| 4,959,606 A | 9/1990 | Forge | | 5,423,810 A | 6/1995 | Goble et al. |
| 4,961,047 A | 10/1990 | Carder | | 5,425,704 A | 6/1995 | Sakurai et al. |
| 4,961,435 A | 10/1990 | Kitagawa et al. | | 5,430,434 A | 7/1995 | Lederer et al. |
| 4,966,597 A | 10/1990 | Cosman | | 5,432,459 A | 7/1995 | Thompson |
| RE33,420 E | 11/1990 | Sussman | | 5,433,739 A | 7/1995 | Sluijter et al. |
| 4,969,885 A | 11/1990 | Farin | | 5,434,398 A | 7/1995 | Goldberg |
| 4,992,719 A | 2/1991 | Harvey | | 5,436,566 A | 7/1995 | Thompson |
| 4,993,430 A | 2/1991 | Shimoyama et al. | | 5,438,302 A | 8/1995 | Goble |
| 4,995,877 A | 2/1991 | Ams et al. | | 5,443,463 A | 8/1995 | Stern et al. |
| 5,015,227 A | 5/1991 | Broadwin et al. | | 5,445,635 A | 8/1995 | Denen |
| 5,019,176 A | 5/1991 | Brandhorst, Jr. | | 5,451,224 A | 9/1995 | Goble et al. |
| 5,024,668 A | 6/1991 | Peters et al. | | 5,458,597 A | 10/1995 | Edwards et al. |
| 5,029,588 A | 7/1991 | Yock et al. | | 5,462,521 A | 10/1995 | Brucker et al. |
| 5,087,257 A | 2/1992 | Farin | | 5,472,441 A | 12/1995 | Edwards et al. |
| 5,099,840 A | 3/1992 | Goble et al. | | 5,472,443 A | 12/1995 | Cordis et al. |
| 5,103,804 A | 4/1992 | Abele et al. | | 5,478,303 A | 12/1995 | Folry-Nolan et al. |
| 5,108,389 A | 4/1992 | Cosmescu | | 5,480,399 A | 1/1996 | Hebborn |
| 5,108,391 A | 4/1992 | Flachenecker | | 5,483,952 A | 1/1996 | Aranyi |
| 5,122,137 A | 6/1992 | Lennox | | 5,490,850 A | 2/1996 | Ellman et al. |
| 5,133,711 A | 7/1992 | Hagen | | 5,496,312 A | 3/1996 | Klicek |
| 5,151,102 A | 9/1992 | Kamiyama et al. | | 5,496,313 A | 3/1996 | Gentelia et al. |
| 5,152,762 A | 10/1992 | McElhenney | | 5,500,012 A | 3/1996 | Brucker et al. |
| 5,157,603 A | 10/1992 | Scheller et al. | | 5,500,616 A | 3/1996 | Ochi |
| 5,160,334 A | 11/1992 | Billings et al. | | 5,514,129 A | 5/1996 | Smith |
| 5,162,217 A | 11/1992 | Hartman | | 5,520,684 A | 5/1996 | Imran |
| 5,167,658 A | 12/1992 | Ensslin | | 5,531,774 A | 7/1996 | Schulman et al. |
| 5,190,517 A | 3/1993 | Zieve et al. | | 5,534,018 A | 7/1996 | Wahlstrand et al. |
| 5,196,008 A | 3/1993 | Kuenecke | | 5,536,267 A | 7/1996 | Edwards et al. |
| 5,196,009 A | 3/1993 | Kirwan, Jr. | | 5,540,677 A * | 7/1996 | Sinofsky ........................ 606/8 |
| 5,201,900 A | 4/1993 | Nardella | | 5,540,681 A | 7/1996 | Strul et al. |
| 5,207,691 A | 5/1993 | Nardella | | 5,540,683 A | 7/1996 | Ichikawa |
| 5,230,623 A | 7/1993 | Guthrie et al. | | 5,540,684 A | 7/1996 | Hassler, Jr. |
| 5,233,515 A | 8/1993 | Cosman | | 5,540,724 A | 7/1996 | Cox |
| 5,249,121 A | 9/1993 | Baum et al. | | 5,556,396 A | 9/1996 | Cohen et al. |
| 5,254,117 A | 10/1993 | Rigby et al. | | 5,558,671 A | 9/1996 | Yates |
| RE34,432 E | 11/1993 | Bertrand | | 5,569,242 A | 10/1996 | Lax et al. |
| 5,267,994 A | 12/1993 | Gentelia et al. | | 5,571,147 A | 11/1996 | Sluijter et al. |
| 5,267,997 A | 12/1993 | Farin | | 5,573,533 A | 11/1996 | Strul |
| 5,281,213 A | 1/1994 | Milder et al. | | 5,584,830 A | 12/1996 | Ladd et al. |
| 5,300,068 A | 4/1994 | Rosar et al. | | 5,588,432 A | 12/1996 | Crowley |
| 5,300,070 A | 4/1994 | Gentelia | | 5,594,636 A | 1/1997 | Schauder |
| 5,318,563 A | 6/1994 | Malis et al. | | 5,596,466 A | 1/1997 | Ochi |
| 5,323,778 A | 6/1994 | Kandarpa et al. | | 5,599,344 A | 2/1997 | Paterson |
| 5,324,283 A | 6/1994 | Heckele | | 5,599,345 A | 2/1997 | Edwards et al. |
| 5,330,518 A | 7/1994 | Neilson et al. | | 5,599,348 A | 2/1997 | Gentelia et al. |
| 5,334,183 A | 8/1994 | Wuchinich | | 5,605,150 A | 2/1997 | Radons et al. |

| | | | | | |
|---|---|---|---|---|---|
| 5,613,966 A | 3/1997 | Makower et al. | 6,044,283 A | 3/2000 | Fein et al. |
| 5,613,996 A | 3/1997 | Lindsay | 6,053,910 A | 4/2000 | Fleenor |
| 5,625,370 A | 4/1997 | D'Hont | 6,053,912 A | 4/2000 | Panescu et al. |
| 5,626,575 A | 5/1997 | Crenner | 6,055,458 A | 4/2000 | Cochran et al. |
| 5,628,745 A | 5/1997 | Bek | 6,056,745 A | 5/2000 | Panescu et al. |
| 5,643,330 A | 7/1997 | Holsheimer et al. | 6,056,746 A | 5/2000 | Goble et al. |
| 5,647,869 A | 7/1997 | Goble et al. | 6,063,075 A | 5/2000 | Mihori |
| 5,647,871 A | 7/1997 | Levine et al. | 6,063,078 A | 5/2000 | Wittkampf |
| 5,651,780 A | 7/1997 | Jackson et al. | 6,068,627 A | 5/2000 | Orszulak et al. |
| 5,658,322 A | 8/1997 | Fleming | 6,074,386 A | 6/2000 | Goble et al. |
| 5,660,567 A | 8/1997 | Nierlich et al. | 6,074,388 A | 6/2000 | Tockweiler et al. |
| 5,674,217 A | 10/1997 | Wahlstrom et al. | 6,080,149 A | 6/2000 | Huang et al. |
| 5,685,840 A | 11/1997 | Schechter et al. | 6,093,186 A | 7/2000 | Goble |
| 5,688,267 A | 11/1997 | Panescu et al. | 6,102,497 A | 8/2000 | Ehr et al. |
| 5,690,692 A | 11/1997 | Fleming | RE36,871 E | 9/2000 | Epstein |
| 5,693,042 A | 12/1997 | Boiarski et al. | 6,113,591 A | 9/2000 | Whayne et al. |
| 5,694,304 A | 12/1997 | Telefus et al. | 6,113,596 A | 9/2000 | Hooven |
| 5,695,494 A | 12/1997 | Becker | 6,123,702 A | 9/2000 | Swanson et al. |
| 5,696,351 A | 12/1997 | Benn et al. | 6,132,429 A | 10/2000 | Baker |
| 5,696,441 A | 12/1997 | Mak et al. | 6,142,992 A | 11/2000 | Cheng et al. |
| 5,702,386 A | 12/1997 | Stern et al. | 6,155,975 A | 12/2000 | Urich et al. |
| 5,702,429 A | 12/1997 | King | 6,162,217 A | 12/2000 | Kannenberg et al. |
| 5,707,369 A | 1/1998 | Vaitekunas et al. | 6,171,304 B1 | 1/2001 | Netherly et al. |
| 5,712,772 A | 1/1998 | Telefus et al. | 6,188,211 B1 | 2/2001 | Rincon-Mora et al. |
| 5,713,896 A | 2/1998 | Nardella | 6,203,541 B1 | 3/2001 | Keppel |
| 5,718,246 A | 2/1998 | Vona | 6,210,403 B1 | 4/2001 | Klicek |
| 5,720,744 A | 2/1998 | Eggleston et al. | 6,222,356 B1 | 4/2001 | Taghizadeh-Kaschani |
| 5,722,975 A | 3/1998 | Edwards et al. | 6,228,080 B1 | 5/2001 | Gines |
| 5,729,448 A | 3/1998 | Haynie et al. | 6,228,081 B1 | 5/2001 | Goble |
| 5,733,281 A | 3/1998 | Nardella | 6,231,569 B1 | 5/2001 | Bek |
| 5,749,869 A | 5/1998 | Lindenmeier et al. | 6,235,020 B1 | 5/2001 | Cheng et al. |
| 5,749,871 A | 5/1998 | Hood et al. | 6,238,387 B1 | 5/2001 | Miller, III |
| 5,755,715 A | 5/1998 | Stern | 6,238,388 B1 | 5/2001 | Ellman |
| 5,762,609 A * | 6/1998 | Benaron et al. ............. 600/473 | 6,241,725 B1 | 6/2001 | Cosman |
| 5,766,165 A | 6/1998 | Gentelia et al. | 6,245,065 B1 | 6/2001 | Panescu |
| 5,769,847 A | 6/1998 | Panescu | 6,246,912 B1 | 6/2001 | Sluijter et al. |
| 5,772,659 A | 6/1998 | Becker et al. | 6,251,106 B1 | 6/2001 | Becker et al. |
| 5,792,138 A | 8/1998 | Shipp | 6,258,085 B1 | 7/2001 | Eggleston |
| 5,797,802 A | 8/1998 | Nowak | 6,261,285 B1 | 7/2001 | Novak |
| 5,797,902 A | 8/1998 | Netherly | 6,261,286 B1 | 7/2001 | Goble et al. |
| 5,814,092 A | 9/1998 | King | 6,273,886 B1 | 8/2001 | Edwards |
| 5,817,093 A | 10/1998 | Williamson, IV et al. | 6,275,786 B1 | 8/2001 | Daners |
| 5,820,568 A | 10/1998 | Willis | 6,293,941 B1 | 9/2001 | Strul |
| 5,827,271 A | 10/1998 | Bussey et al. | 6,293,942 B1 | 9/2001 | Goble et al. |
| 5,830,212 A | 11/1998 | Cartmell | 6,296,636 B1 | 10/2001 | Cheng et al. |
| 5,836,909 A | 11/1998 | Cosmescu | 6,306,131 B1 | 10/2001 | Hareyama et al. |
| 5,836,943 A | 11/1998 | Miller, III | 6,306,134 B1 | 10/2001 | Goble et al. |
| 5,836,990 A | 11/1998 | Li | 6,309,386 B1 | 10/2001 | Bek |
| 5,846,236 A | 12/1998 | Lindenmeier et al. | 6,325,799 B1 | 12/2001 | Goble |
| 5,868,737 A | 2/1999 | Taylor et al. | 6,337,998 B1 | 1/2002 | Behl et al. |
| 5,868,739 A | 2/1999 | Lindenmeier et al. | 6,338,657 B1 | 1/2002 | Harper et al. |
| 5,868,740 A | 2/1999 | LeVeen et al. | 6,350,262 B1 | 2/2002 | Ashley |
| 5,871,481 A | 2/1999 | Kannenberg et al. | 6,358,245 B1 | 3/2002 | Edwards |
| 5,897,552 A | 4/1999 | Edwards et al. | 6,364,877 B1 | 4/2002 | Goble et al. |
| 5,908,444 A | 6/1999 | Azure | 6,383,183 B1 | 5/2002 | Sekino et al. |
| 5,913,882 A | 6/1999 | King | 6,391,024 B1 | 5/2002 | Sun et al. |
| 5,921,982 A | 7/1999 | Lesh et al. | 6,398,779 B1 | 6/2002 | Buysse et al. |
| 5,925,070 A | 7/1999 | King et al. | 6,398,781 B1 | 6/2002 | Goble et al. |
| 5,931,836 A | 8/1999 | Hatta et al. | 6,402,741 B1 | 6/2002 | Keppel et al. |
| 5,938,690 A | 8/1999 | Law et al. | 6,402,743 B1 | 6/2002 | Orszulak et al. |
| 5,948,007 A | 9/1999 | Starkebaum et al. | 6,416,509 B1 | 7/2002 | Goble et al. |
| 5,951,545 A | 9/1999 | Schilling | 6,436,096 B1 | 8/2002 | Hareyama |
| 5,951,546 A | 9/1999 | Lorentzen | 6,451,015 B1 | 9/2002 | Rittman, III et al. |
| 5,954,686 A | 9/1999 | Garito et al. | 6,458,121 B1 | 10/2002 | Rosenstock |
| 5,954,717 A | 9/1999 | Behl et al. | 6,464,689 B1 | 10/2002 | Qin |
| 5,954,719 A | 9/1999 | Chen et al. | 6,464,696 B1 | 10/2002 | Oyama |
| 5,961,344 A | 10/1999 | Rosales et al. | 6,498,466 B1 | 12/2002 | Edwards |
| 5,971,980 A | 10/1999 | Sherman | 6,506,189 B1 | 1/2003 | Rittman, III et al. |
| 5,976,128 A | 11/1999 | Schilling et al. | 6,508,815 B1 | 1/2003 | Strul |
| 5,983,141 A | 11/1999 | Sluijter et al. | 6,511,476 B2 | 1/2003 | Hareyama |
| 6,010,499 A | 1/2000 | Cobb | 6,511,478 B1 | 1/2003 | Burnside et al. |
| 6,014,581 A | 1/2000 | Whayne et al. | 6,517,538 B1 | 2/2003 | Jacob et al. |
| 6,033,399 A | 3/2000 | Gines | 6,524,308 B1 | 2/2003 | Muller et al. |

| | | |
|---|---|---|
| 6,547,786 B1 | 4/2003 | Goble |
| 6,558,376 B2 | 5/2003 | Bishop |
| 6,560,470 B1 * | 5/2003 | Pologe .................. 600/310 |
| 6,562,037 B2 | 5/2003 | Paton |
| 6,565,559 B2 | 5/2003 | Eggleston |
| 6,573,248 B2 | 6/2003 | Ramasamy et al. |
| 6,575,969 B1 | 6/2003 | Rittman, III et al. |
| 6,582,427 B1 | 6/2003 | Goble et al. |
| 6,620,157 B1 | 9/2003 | Dabney et al. |
| 6,623,423 B2 | 9/2003 | Sakurai et al. |
| 6,629,973 B1 * | 10/2003 | Wårdell et al. ................ 606/40 |
| 6,635,057 B2 | 10/2003 | Harano |
| 6,645,198 B1 | 11/2003 | Bommannan et al. |
| 6,648,883 B2 | 11/2003 | Francischelli |
| 6,652,514 B2 | 11/2003 | Ellman |
| 6,663,623 B1 | 12/2003 | Oyama et al. |
| 6,663,624 B2 | 12/2003 | Edwards |
| 6,666,860 B1 | 12/2003 | Takahashi |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim |
| 6,693,782 B1 | 2/2004 | Lash |
| 6,712,813 B2 | 3/2004 | Ellman |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,755,825 B2 | 6/2004 | Shoenman et al. |
| 6,758,846 B2 | 7/2004 | Goble et al. |
| 6,783,523 B2 | 8/2004 | Qin |
| 6,786,905 B2 | 9/2004 | Swanson et al. |
| 6,790,206 B2 | 9/2004 | Panescu |
| 6,796,981 B2 | 9/2004 | Wham |
| 6,824,539 B2 | 11/2004 | Novak |
| 6,830,569 B2 | 12/2004 | Thompson |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,893,435 B2 | 5/2005 | Roane |
| 6,923,804 B2 | 8/2005 | Eggers et al. |
| 6,929,641 B2 | 8/2005 | Goble et al. |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,966,907 B2 | 11/2005 | Goble |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,381 B2 | 2/2006 | Harano et al. |
| 7,004,174 B2 | 2/2006 | Eggers et al. |
| 7,041,096 B2 | 5/2006 | Malis et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,122,031 B2 | 10/2006 | Edwards et al. |
| 7,131,860 B2 | 11/2006 | Sartor et al. |
| 7,137,980 B2 | 11/2006 | Buysse et al. |
| 7,147,638 B2 | 12/2006 | Chapman et al. |
| 7,160,293 B2 | 1/2007 | Sturm et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,211,081 B2 | 5/2007 | Goble |
| 7,214,224 B2 | 5/2007 | Goble |
| 7,220,260 B2 | 5/2007 | Fleming et al. |
| 7,247,155 B2 | 7/2007 | Hoey et al. |
| 7,250,746 B2 | 7/2007 | Oswald et al. |
| 7,255,694 B2 | 8/2007 | Keppel |
| 7,282,048 B2 | 10/2007 | Goble et al. |
| 7,300,435 B2 | 11/2007 | Wham et al. |
| 7,303,557 B2 | 12/2007 | Wham et al. |
| 7,364,577 B2 | 4/2008 | Wham et al. |
| 7,367,972 B2 | 5/2008 | Francischelli et al. |
| RE40,388 E | 6/2008 | Gines |
| 7,396,336 B2 | 7/2008 | Orszulak et al. |
| 2001/0014804 A1 | 8/2001 | Goble et al. |
| 2001/0029315 A1 | 10/2001 | Sakurai et al. |
| 2001/0031962 A1 | 10/2001 | Eggleston |
| 2002/0035363 A1 | 3/2002 | Edwards et al. |
| 2002/0035364 A1 | 3/2002 | Schoenman et al. |
| 2002/0052599 A1 | 5/2002 | Goble |
| 2002/0068932 A1 | 6/2002 | Edwards |
| 2002/0107517 A1 | 8/2002 | Witt et al. |
| 2002/0111624 A1 | 8/2002 | Witt et al. |
| 2002/0151889 A1 | 10/2002 | Swanson et al. |
| 2002/0193787 A1 | 12/2002 | Qin |
| 2003/0004510 A1 | 1/2003 | Wham et al. |
| 2003/0060818 A1 | 3/2003 | Kannenberg |
| 2003/0078572 A1 | 4/2003 | Pearson et al. |
| 2003/0139741 A1 | 7/2003 | Goble et al. |
| 2003/0153908 A1 | 8/2003 | Goble |
| 2003/0163123 A1 | 8/2003 | Goble |
| 2003/0163124 A1 | 8/2003 | Goble |
| 2003/0171745 A1 | 9/2003 | Francischelli |
| 2003/0181898 A1 | 9/2003 | Bowers |
| 2003/0199863 A1 | 10/2003 | Swanson |
| 2003/0225401 A1 | 12/2003 | Eggers et al. |
| 2004/0002745 A1 | 1/2004 | Fleming |
| 2004/0006333 A1 * | 1/2004 | Arnold et al. .................. 606/15 |
| 2004/0015159 A1 * | 1/2004 | Slater et al. .................. 606/32 |
| 2004/0015163 A1 | 1/2004 | Buysse et al. |
| 2004/0015216 A1 | 1/2004 | DeSisto |
| 2004/0019347 A1 | 1/2004 | Sakurai |
| 2004/0024395 A1 | 2/2004 | Ellman |
| 2004/0030328 A1 | 2/2004 | Eggers |
| 2004/0030330 A1 | 2/2004 | Brassell et al. |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm et al. |
| 2004/0068304 A1 | 4/2004 | Paton |
| 2004/0082946 A1 | 4/2004 | Malis |
| 2004/0095100 A1 | 5/2004 | Thompson |
| 2004/0097912 A1 | 5/2004 | Gonnering |
| 2004/0097914 A1 | 5/2004 | Pantera |
| 2004/0097915 A1 | 5/2004 | Refior |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0143263 A1 | 7/2004 | Schechter et al. |
| 2004/0147918 A1 | 7/2004 | Keppel |
| 2004/0167508 A1 | 8/2004 | Wham et al. |
| 2004/0172016 A1 | 9/2004 | Bek |
| 2004/0193148 A1 | 9/2004 | Wham et al. |
| 2004/0230189 A1 | 11/2004 | Keppel |
| 2004/0243120 A1 | 12/2004 | Orszulak et al. |
| 2004/0260279 A1 | 12/2004 | Goble |
| 2005/0004564 A1 | 1/2005 | Wham |
| 2005/0004569 A1 | 1/2005 | Witt et al. |
| 2005/0021020 A1 | 1/2005 | Blaha et al. |
| 2005/0021022 A1 | 1/2005 | Sturm et al. |
| 2005/0101949 A1 | 5/2005 | Harano et al. |

| | | | | | | |
|---|---|---|---|---|---|---|
| 2005/0101951 | A1 | 5/2005 | Wham | EP | 836868 | 4/1998 |
| 2005/0113818 | A1 | 5/2005 | Sartor | EP | 878169 | 11/1998 |
| 2005/0113819 | A1 | 5/2005 | Wham | EP | 1051948 | 11/2000 |
| 2005/0149151 | A1 | 7/2005 | Orszulak | EP | 1053720 | 11/2000 |
| 2005/0182398 | A1 | 8/2005 | Paterson | EP | 1151725 | 11/2001 |
| 2005/0197659 | A1 | 9/2005 | Bahney | EP | 1293171 | 3/2003 |
| 2005/0203504 | A1 | 9/2005 | Wham et al. | EP | 1472984 | 11/2004 |
| 2005/0251117 | A1* | 11/2005 | Anderson et al. ............... 606/9 | EP | 1495712 | 1/2005 |
| 2006/0025760 | A1 | 2/2006 | Podhajsky | EP | 1500378 | 1/2005 |
| 2006/0079871 | A1 | 4/2006 | Plaven et al. | EP | 1535581 | 6/2005 |
| 2006/0161148 | A1 | 7/2006 | Behnke | EP | 1609430 | 12/2005 |
| 2006/0178664 | A1 | 8/2006 | Keppel | EP | 1645235 | 4/2006 |
| 2006/0224152 | A1 | 10/2006 | Behnke et al. | EP | 0880220 B1 | 6/2006 |
| 2006/0281360 | A1 | 12/2006 | Sartor et al. | EP | 1707143 | 10/2006 |
| 2007/0038209 | A1 | 2/2007 | Buysse et al. | EP | 1810633 | 6/2007 |
| 2007/0093800 | A1 | 4/2007 | Wham et al. | EP | 1810628 | 7/2007 |
| 2007/0093801 | A1 | 4/2007 | Behnke | EP | 1810630 | 7/2007 |
| 2007/0135812 | A1 | 6/2007 | Sartor | FR | 1275415 | 10/1961 |
| 2007/0173802 | A1 | 7/2007 | Keppel | FR | 1347865 | 11/1963 |
| 2007/0173803 | A1 | 7/2007 | Wham et al. | FR | 2313708 | 12/1976 |
| 2007/0173804 | A1 | 7/2007 | Wham et al. | FR | 2502935 | 10/1982 |
| 2007/0173805 | A1 | 7/2007 | Weinberg et al. | FR | 2517953 | 6/1983 |
| 2007/0173806 | A1 | 7/2007 | Orszulak et al. | FR | 2573301 | 5/1986 |
| 2007/0173810 | A1 | 7/2007 | Orszulak | GB | 607850 | 9/1948 |
| 2007/0173813 | A1 | 7/2007 | Odom | GB | 855459 | 11/1960 |
| 2007/0208339 | A1 | 9/2007 | Arts et al. | GB | 902775 | 8/1962 |
| 2007/0225698 | A1 | 9/2007 | Orszulak et al. | GB | 2164473 | 3/1986 |
| 2007/0250052 | A1 | 10/2007 | Wham | GB | 2214430 | 9/1989 |
| 2007/0265612 | A1 | 11/2007 | Behnke et al. | GB | 2358934 A | 8/2001 |
| 2007/0282320 | A1 | 12/2007 | Buysse et al. | SU | 166452 | 1/1965 |
| 2007/0287998 | A1* | 12/2007 | Sharareh et al. ............... 606/41 | SU | 727201 | 4/1980 |
| 2008/0015564 | A1 | 1/2008 | Wham et al. | WO | WO92/06642 | 4/1992 |
| 2008/0039831 | A1 | 2/2008 | Odom et al. | WO | WO93/24066 | 12/1993 |
| 2008/0039836 | A1 | 2/2008 | Odom et al. | WO | WO94/24949 | 11/1994 |
| 2008/0082094 | A1 | 4/2008 | McPherson et al. | WO | WO94/28809 | 12/1994 |
| 2008/0125767 | A1 | 5/2008 | Blaha | WO | WO95/09577 | 4/1995 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 A1 | 5/1995 |
| DE | 19717411 | 11/1998 |
| DE | 19848540 A1 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 0569130 A1 | 11/1993 |
| EP | 608609 | 8/1994 |
| EP | 694291 | 1/1996 |
| WO | WO95/19148 | 7/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO02/011634 | 2/2002 |
| WO | WO 02 16634 | 2/2002 |
| WO | WO02/045589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/092520 | 11/2003 |
| WO | WO2003/090635 | 11/2003 |
| WO | WO2004/028385 | 4/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005048809 A1 | 6/2005 |
| WO | WO2005/060849 | 7/2005 |

OTHER PUBLICATIONS

International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.
International Search Report EP07004355.9 dated May 21, 2007.

Muller et al., "Extended Left Hemicolectomy Using the LigaSure Vessel Sealing System" Innovations That Work; Sep. 1999.
International Search Report EP 07008207.8 dated Sep. 5, 2007.
International Search Report EP 07010673.7 dated Sep. 24, 2007.
International Search Report EP 06000708.5 dated Apr. 21, 2006.
International Search Report—Extended EP 06000708.5 dated Aug. 22, 2006.
International Search Report EP 05002769.7 dated Jun. 9, 2006.
International Search Report EP 06006717.0 dated Aug. 7, 2006.
Ni W et al: "A Signal Processing Method for the Coriolis Mass Flowmeter Based on a Normalized . . ." Journal of Applied Sciences—Yingyong Kexue Xuebao, Shanghai CN, vol. 23 No. 2;(Mar. 2005); 160-164.
Medtrex Brochure "The O.R. Pro 300" 1 p. Sep. 1998.
Valleylab Brochure "Valleylab Electroshield Monitoring System" 2 pp. Nov. 1995.
Richard Wolf Medical Instruments Corp. Brochure, "Kleppinger Bipolar Forceps & Bipolar Generator" 3 pp. Jan. 1989.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
Alexander at al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic computerized Bipolar Coagulator" Journal of Neurosurgery 75:1, (Jul. 1991) pp. 148-151.
Chicharo et al. "A Sliding Goertzel Algorith" Aug. 1996, pp. 283-297 Signal Processing, Elsevier Science Publishers B.V. Amsterdam, NL vol. 52 No. 3.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedence" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Ogden Goertzel Alternative to the Fourier Transform: Jun. 1993 pp. 485-487 Electronic World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Vallfors et al., "Automatically Controlled Bipolar Electrosoagulation-'COA-COMP" Neurosurgical Review 7:2-3 (1984) pp. 187-190.
Wald et al., "Accidental Burns", JAMA, Aug. 16, 1971, vol. 217, No. 7, pp. 916-921.
International Search Report dated July 3, 2003.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.

* cited by examiner

METHOD AND SYSTEM FOR OPTICALLY DETECTING BLOOD AND CONTROLLING A GENERATOR DURING ELECTROSURGERY

PRIORITY

This application claims priority to a U.S. Provisional Application filed on May 6, 2002 and assigned U.S. Provisional Application Ser. No. 60/378,290, the entire contents of which are incorporated herein by reference.

BACKGROUND

1. Technical Field

The disclosure relates to electrosurgery combined with optical detection of blood, and more particularly the automatic control of the level of electrosurgical energy to be delivered to tissue in accordance with the amount of blood optically detected.

2. Description of the Related Art

Electrosurgery involves the application of radio frequency energy to achieve a tissue effect. An electrosurgical generator is used in surgical procedures to deliver electrical energy to the tissue of a patient. An electrosurgical generator often includes a radio frequency generator and its controls. When an electrode is connected to the generator, the electrode can be used for cutting or coagulating the tissue of a patient with high frequency electrical energy. During normal operation, alternating electrical current from the generator flows between an active electrode and a return electrode by passing through the tissue and bodily fluids of a patient.

The electrical energy usually has its waveform shaped to enhance its ability to cut or coagulate tissue. Different waveforms correspond to different modes of operation of the generator, and each mode gives the surgeon various operating advantages. Modes may include cut, coagulate, a blend thereof, or desiccate. A surgeon can easily select and change the different modes of operation as the surgical procedure progresses.

In each mode of operation, it is important to regulate the electrosurgical energy delivered to the patient to achieve the desired surgical effect. This can be done, for example, by controlling the output energy from the electrosurgical generator for the type of tissue being treated.

Different types of tissues will be encountered as the surgical procedure progresses and each unique tissue requires more or less energy in terms of voltage, current or power as a function of frequently changing tissue impedance and other factors, such as the level of vascularization, i.e., blood flow within the tissue. Therefore, the same tissue will present different load impedance as the tissue is desiccated.

Two conventional types of energy regulation are used in commercial electrosurgical generators. The most common type controls the DC power supply of the generator by limiting the amount of power provided from the AC mains to which the generator is connected. A feedback control loop regulates output voltage by comparing a desired voltage or current with the output voltage or current supplied by the power supply. Another type of power regulation in commercial electrosurgical generators controls the gain of the high-frequency or radio frequency amplifier. A feedback control loop compares the output power supplied from the RF amplifier for adjustment to a desired power level.

U.S. Pat. Nos. 3,964,487; 3,980,085; 4,188,927 and 4,092,986 have circuitry to reduce the output current in accordance with increasing load impedance. In those patents, constant voltage output is maintained and the current is decreased with increasing load impedance.

U.S. Pat. No. 4,126,137 controls the power amplifier of the electrosurgical unit in accord with a non-linear compensation circuit applied to a feedback signal derived from a comparison of the power level reference signal and the mathematical product of two signals including sensed current and voltage in the unit.

U.S. Pat. No. 4,658,819 has an electrosurgical generator which has a microprocessor controller based means for decreasing the output power as a function of changes in tissue impedance.

U.S. Pat. No. 4,727,874 includes an electrosurgical generator with a high frequency pulse width modulated feedback power control wherein each cycle of the generator is regulated in power content by modulating the width of the driving energy pulses.

U.S. Pat. No. 3,601,126 has an electrosurgical generator having a feedback circuit that attempts to maintain the output current at constant amplitude over a wide range of tissue impedances.

None of the aforementioned U.S. patents include optical detection of blood for regulating or controlling the output energy or output waveforms of the electrosurgical generator during different operational modes over a finite patient tissue impedance range. Optical detection of blood during electrosurgery also allows surgeons with color blindness to effectively perform electrosurgery. In a study that was published in 1997, 18 of 40 physicians with color blindness reported difficulties in detecting blood in body products. Spalding, J. Anthony B., "Doctors with inherited colour vision deficiency: their difficulties in clinical work," Cavonius C R, ed., Colour Vision Deficiencies, XII: Proceeding of the International Research Group for Colour Vision Deficiencies, 1995, Norwell, Mass.: Kluwer Academic Publishers, pages 483-489, 1997.

Accordingly, there exists a need for a method and system for optically detecting blood during electrosurgery and controlling the output energy or output waveforms of an electrosurgical generator in accordance with the amount of blood optically detected.

SUMMARY

A method and electrosurgical system for optically detecting blood and controlling an electrosurgical generator are provided. An optical blood detection system is used for optically detecting blood and may be included as an integral part of the overall electrosurgical system's circuitry, or may be designed as a separate unit that connects to, and controls, an electrosurgical generator. The optical blood detection system may be embodied through a variety of analog, digital and/or optical circuit components or arrangements, including software running on computational and memory circuitry.

The optical blood detection system controls the output energy of the electrosurgical generator in accordance with the amount of blood detected. This allows for a surgeon to perform electrosurgery without having to stop and observe the condition of the tissue to determine if additional electrosurgery is needed.

More particularly, the optical blood detection system automatically controls the output waveform generated by the electrosurgical generator during electrosurgery using a feedback signal received from the optical blood detection system. For example, if coagulation of the tissue is desired, the optical blood detection system continuously analyzes the tissue for the presence of blood and controls the output waveform accordingly.

While the optical blood detection system may be used to control electrosurgical generators of varying designs, it is preferred that the electrosurgical generator includes a power selection system wherein the user may initialize, set, monitor, and/or control the operation of the electrosurgical generator. The preferred electrosurgical generator need not be limited to these four functional elements, for example the electrosurgical generator could also include additional safety, monitoring, signal modification/conditioning, and/or feedback circuitry or functional elements/processes. The actual electrosurgical generator's design may include the use of digital components and signaling, analog components and signaling, and/or optical components and signaling, or may be embodied, completely or partially within a software process running on hardware components.

The optical blood detection system includes an optical light beam generating circuit having optical components for generating and focusing a light beam in close proximity to and/or on an electrode of an electrosurgical instrument; a circuit having optical components for capturing reflected light energy, such as a photosensitive detector; a blood detection circuit for analyzing the reflected light energy and/or other characteristics and determining the amount of blood present in proximity to and/or on the electrode; and a feedback correction circuit.

The feedback correction circuit which is electrically connected to receive a signal from the blood detection circuit functions to produce a feedback control signal which it then supplies to the power selection system, within the electrosurgical generator, so as to cause the power selection system to control the amount of electrosurgical energy created and/or the type of output waveform generated in accordance to the amount of blood present in proximity to and/or on the electrode. The system can also detect the presence of any blood vessels in proximity to the distal end of the electrode and control the electrosurgical generator accordingly or alert the surgeon to prevent, for example, the severing of major blood vessels.

Preferably, the optical light beam is focused in front of the distal end of the electrode to detect blood present on tissue which is being cut or coagulated by the electrosurgical instrument. The optical light beam may have light energy within the visible, near-infrared and infrared light spectrum wavelengths.

It is provided that one or more of the above-mentioned circuits can be implemented by one or more sets of programmable instructions configured for being executed by at least one processor of the electrosurgical system or at least one processor remotely located from the electrosurgical system. For example, the data corresponding to the reflected light energy can be transmitted, either wirelessly or non-wirelessly, over a network, such as a LAN, WAN, or the Internet, to a remote server or control station for analyzing the data using a set of programmable instructions for determining the amount of blood present in proximity to and/or on the electrode.

In accordance with the analysis performed, the remote server or control station then generates using the same or another set of programmable instructions the feedback control signal and supplies the signal to the power selection system. It is contemplated that another form of electromagnetic energy can be used to detect for the presence of blood besides the optical beam of light.

In one embodiment of the present invention an electrosurgical system is provided which includes a handpiece having a proximal end and a distal end from which light energy is emitted therefrom; at least one electrosurgical electrode on the handpiece and extending from the distal end from which electrosurgical energy is emitted there from; a source of light energy for generating the light energy and transmitting the same to the distal end via at least one waveguide; a source of electrosurgical energy for generating the electrosurgical energy and transmitting the same by at least one electrically conductive element to the electrode; and means for analyzing light energy characteristics for determining the amount of blood present in proximity to the electrode and for controlling the source of electrosurgical energy accordingly.

In another embodiment of the present invention an electrosurgical system is provided which includes means for generating and directing light energy on tissue; means for generating electrosurgical energy and transmitting the same via an electrode to the tissue; and means for analyzing characteristics of the light energy for determining the amount of blood present in proximity to the electrode and for controlling the means for generating electrosurgical energy accordingly.

Further, in another embodiment of the present invention, a method is provided for performing electrosurgery. The method includes the steps of supplying light energy and electrosurgical energy to tissue via at least one instrument having a distal end; and analyzing characteristics of the light energy for determining the amount of blood present in proximity to the at least one instrument and for controlling the delivery of electrosurgical energy accordingly.

Finally, in another embodiment of the present invention, a surgical method is provided which includes the steps of providing a surgical instrument configured for insertion within a patient; providing a source of light energy for generating light energy and delivering the same via the surgical instrument; and analyzing light energy characteristics for determining the amount of blood present in proximity to the surgical instrument.

Further features of the disclosure will become more readily apparent to those skilled in the art from the following detailed description taken in conjunction with the drawings.

BRIEF DESCRIPTION OF THE DRAWINGS

Various embodiments will be described hereinbelow with reference to the drawings wherein.

DETAILED DESCRIPTION OF A PREFERRED EMBODIMENT

Figure 1:
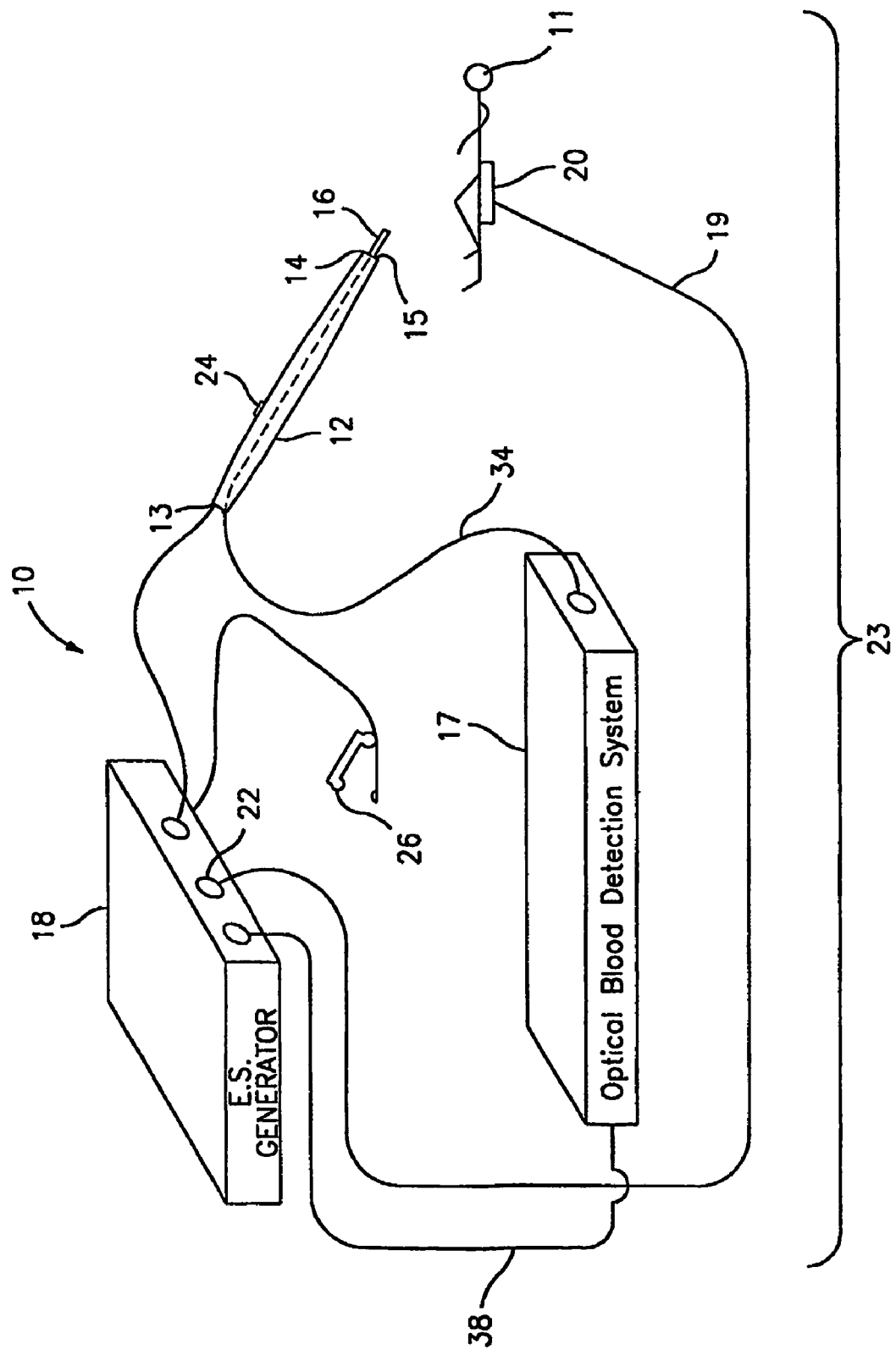
FIG. 1 is a perspective diagram of one embodiment of the present electrosurgical system.

An electrosurgical system 10 is shown in perspective in FIG. 1 and allows a surgeon to provide cutting, coagulating, and/or a combination thereof on tissue of a patient 11. The electrosurgical system 10 has a handpiece 12 with a proximal end 13 to be held and controlled by the surgeon. A distal end 14 on the handpiece 12 has a port 15 from which an optical light beam is directed to the patient 11. An electrosurgical electrode 16 extends from the distal end 14 of the handpiece 12.

An optical blood detection system 17 for generating the optical light beam is connected to the proximal end 13 of the handpiece 12 via waveguide/wires 34. The optical blood detection system 17 can be manually controlled by the surgeon or automatically controlled for delivering the optical light beam from the distal end 14 of the handpiece 12 toward the patient 11. An electrosurgical generator 18 for generating the electrosurgical energy is electrically connected to the proximal end 13 of the handpiece 12 and may be manually controlled by the surgeon or automatically controlled for transmitting electrosurgical energy from the electrosurgical electrode 16 toward the patient 11. The optical blood detection system 17 and the electrosurgical generator 18 are connected by a cable 38 for providing data communications there between and a feedback control signal from the optical blood detection system 17 to the generator 18 for controlling the generator 18.

While the optical blood detection system 17 may be used to control electrosurgical generator 18, it is preferred that the electrosurgical generator 18 includes a power selection system wherein the user may initialize, set, monitor, and/or control the operation of the electrosurgical generator 18. The preferred electrosurgical generator need not be limited to these four functional elements, for example the electrosurgical generator 18 could also include additional safety, monitoring, signal modification/conditioning, and/or feedback circuitry or functional elements/processes. The actual electrosurgical generator's design may include the use of digital components and signaling, analog components and signaling, and/or optical components and signaling, or may be embodied, completely or partially within a software process running on hardware components.

A return path 19 is provided for the electrosurgical energy; the return path 19 may be in a monopolar or bipolar circuit. FIG. 1 illustrates a monopolar circuit having a return pad 20, in lieu of a return electrode in the case of a bipolar circuit. The return path 19 is connected to receive at least a portion of the transmitted electrosurgical energy from the source of electrosurgical energy 18 and then the patient 11. A return input 22 for the source of electrosurgical energy 18 is connected to the return path 19 for furnishing a complete circuit 23 between the electrosurgical electrode 16, the patient 11, and the electrosurgical generator 18.

A manually-actuated control button 24 is provided on the handpiece 12 for the selective control by the surgeon of the electrosurgical generator 18 for controlling the electrosurgical energy delivered from the distal end 14. The control button 24 may also be located at a foot pedal 26.

It is provided that the surgeon can utilize the optical beam emanating from port 15 to pinpoint the target tissue to be treated if the optical light beam has light energy within the visible spectrum. It is envisioned that the optical light beam may have light energy within the visible, near-infrared and infrared light spectrum wavelengths.

Figure 3:
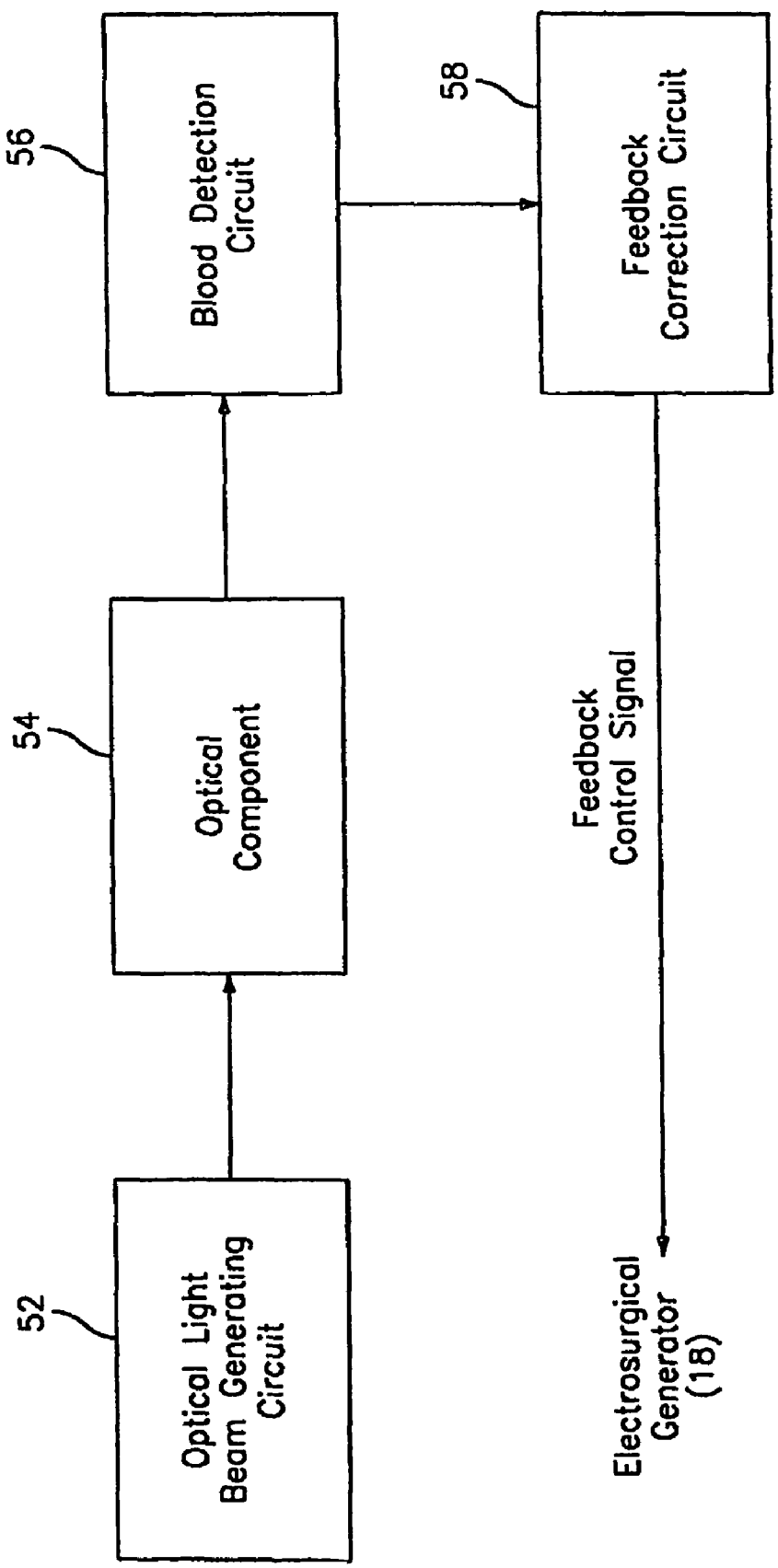
FIG. 3 is a block diagram of the optical blood detection system.

With reference to FIG. 3, the optical blood detection system 17 includes an optical light beam generating circuit 52 having optical components for generating and focusing a light beam, such as a laser light beam, as known in the art, in close proximity to and/or on the electrode 16 of the handpiece 12. The wave guide 34, shown in FIG. 1, is used to deliver the light energy from the proximal end 13 to beyond the distal end 14. The optical blood detection system 17 further includes at least one optical component 54 positioned at the distal end 14 of the handpiece 12, for capturing reflected light energy as known in the art. The at least one optical component 54 returns signals indicative of the reflected light energy to the system 17 via waveguide/wires 34 to at least one photosensitive detector.

The optical blood detection system 17 further includes a blood detection circuit 56 for analyzing the reflected light energy and determining the amount of blood present in proximity to and/or on the electrode 16; and a feedback correction circuit 58.

The reflected light energy preferably includes data corresponding to light reflections indicative of two different wavelengths, a first and a second wavelength. First, a first optical light beam having the first wavelength is generated and emanated from the handpiece 12. The reflected light energy indicative of the first optical light beam is captured and analyzed by the optical blood detection system 17 for measuring various parameters, such as photon counts. Second, a second optical light beam having the second wavelength is generated and emanated from the handpiece 12. The reflected light energy indicative of the second optical light beam is captured and analyzed by the optical blood detection system 17 for measuring various parameters, such as photon counts. Alternatively, a broadband optical light beam is generated and emanated from the handpiece 12. The reflected light energies indicative of two separate and distinct wavelengths are captured and analyzed by the optical blood detection system 17 for measuring various parameters, such as photon counts. Preferably, in either method, the first wavelength is in the range of 620-700 nanometers and the second wavelength is in the range of 540-610 nanometers or 950-1050 nanometers.

A ratio is then obtained using two measured values corresponding to a particular parameter; one measured value is indicative of the first optical light beam or wavelength and one measured value is indicative of the second optical light beam or wavelength. A look-up table or other data structure is then used by a processor or by an individual to correlate the ratio with a particular amount or level of blood present in proximity to the electrode 16.

The reflected light energy can also be analyzed for determining the amount of blood present using one of several known methods, such as Near Infrared Spectroscopy (NIRS), Infrared Spectroscopy (IRS), Fluorescence Spectroscopy, Raman Spectroscopy, Photoacoustic Spectroscopy (where the system 10 is equipped with a microphone for measuring an acoustic pressure wave created by the optical beam rapidly heating the tissue), laser Doppler flowmetry, light scatter change measurements, and polarization change measurements. These methods determine the light intensity level, light scattering effects, level of fluorescent energy, and other characteristics of the reflected light energy. The determined light intensity level, light scattering effects, level of fluorescent energy, and/or other characteristics of the reflected light energy are then used to compute using mathematical equations, algorithms, and/or programmable instructions executed by at least one processor the amount of blood present in proximity to the electrode 16.

By knowing the optical signal characteristics of the generated light beam and the determined light intensity level, light scattering effects, level of fluorescent energy, and other characteristics of the reflected light energy, the system 17 is able to determine using a look-up table or other data structure the amount of blood present in proximity to the electrode 16. If the analysis indicates that there is a high amount of blood present in proximity to the electrode 16, one can conclude that the tissue has not coagulated (in the case of a coagulation procedure) or has been cut (in the case of a cutting procedure). If the analysis indicates that there is a low amount of blood present in proximity to the electrode 16, one can conclude that the tissue has coagulated (in the case of a coagulation procedure) or has not been adequately cut (in the case of a cutting procedure).

The system can also detect the presence of any blood vessels in proximity to the distal end of the electrode 16 and control the electrosurgical generator 18 accordingly or alert the surgeon to prevent, for example, the severing of major blood vessels.

The feedback correction circuit 58 which is electrically connected to receive a signal from the blood detection circuit 56 functions to produce a feedback control signal which it then supplies to the power selection system, within the electrosurgical generator 18, via wire 38 so as to cause the power selection system to control the amount of electrosurgical energy created and/or the type of output waveform generated (coagulation or tissue division waveform) in accordance to the amount of blood present in proximity to and/or on the electrode 16.

Figure 4:
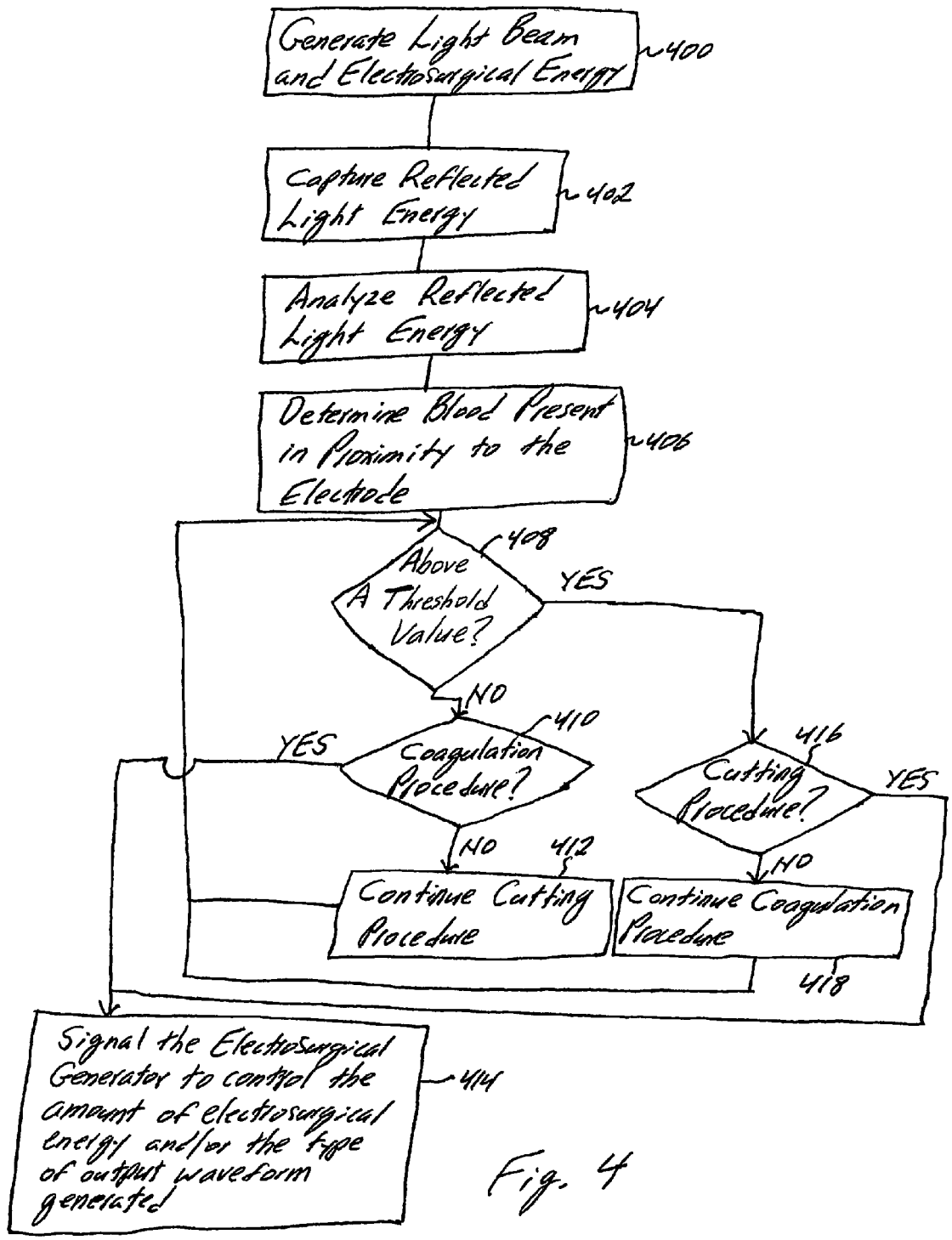
FIG. 4 is a flow chart showing the operation of the optical blood detection system according to a first method.

FIG. 4 is a flow chart illustrating an exemplary method of operation of the optical blood detection system 17. In step 400, the optical light beam and electrosurgical energy are generated. The reflected light energy is captured in step 402 and analyzed in step 404 to determine the amount of blood present in proximity to the electrode 16 at step 406. In step 408 it is determined whether the sensed level of blood in proximity to the electrode 16 is above a predetermined threshold (the predetermined threshold value is dependent on the method being used to detect the amount of blood present). If the sensed level of blood is not above the predetermined threshold value, it is then determined at step 410 whether the procedure being performed is a coagulation procedure. If a coagulation procedure is not being performed, i.e., a cutting procedure is being performed, the cutting procedure is continued at step 412, and the process returns to step 408.

If at step 410, it is determined that a coagulation procedure is being performed, the process proceeds to step 414 where a signal is transmitted by the feedback correction circuit 58 to the electrosurgical generator 18 to control the amount of electrosurgical energy and/or the type of output waveform generated or to shut-off the electrosurgical generator 18, since the coagulation procedure has been adequately performed. If at step 408, it is determined that the sensed level of blood is above the predetermined threshold value, it is then determined at step 416 whether the procedure being performed is a cutting procedure. If a cutting procedure is not being performed, i.e., a coagulation procedure is being performed, the coagulation procedure is continued at step 418, and the process returns to step 408.

If at step 416, it is determined that a cutting procedure is being performed, the process proceeds to step 414 where a signal is transmitted by the feedback correction circuit 58 to the electrosurgical generator 18 to control the amount of electrosurgical energy and/or the type of output waveform generated or to shut-off the electrosurgical generator 18, since the cutting procedure has been adequately performed.

Figure 5:
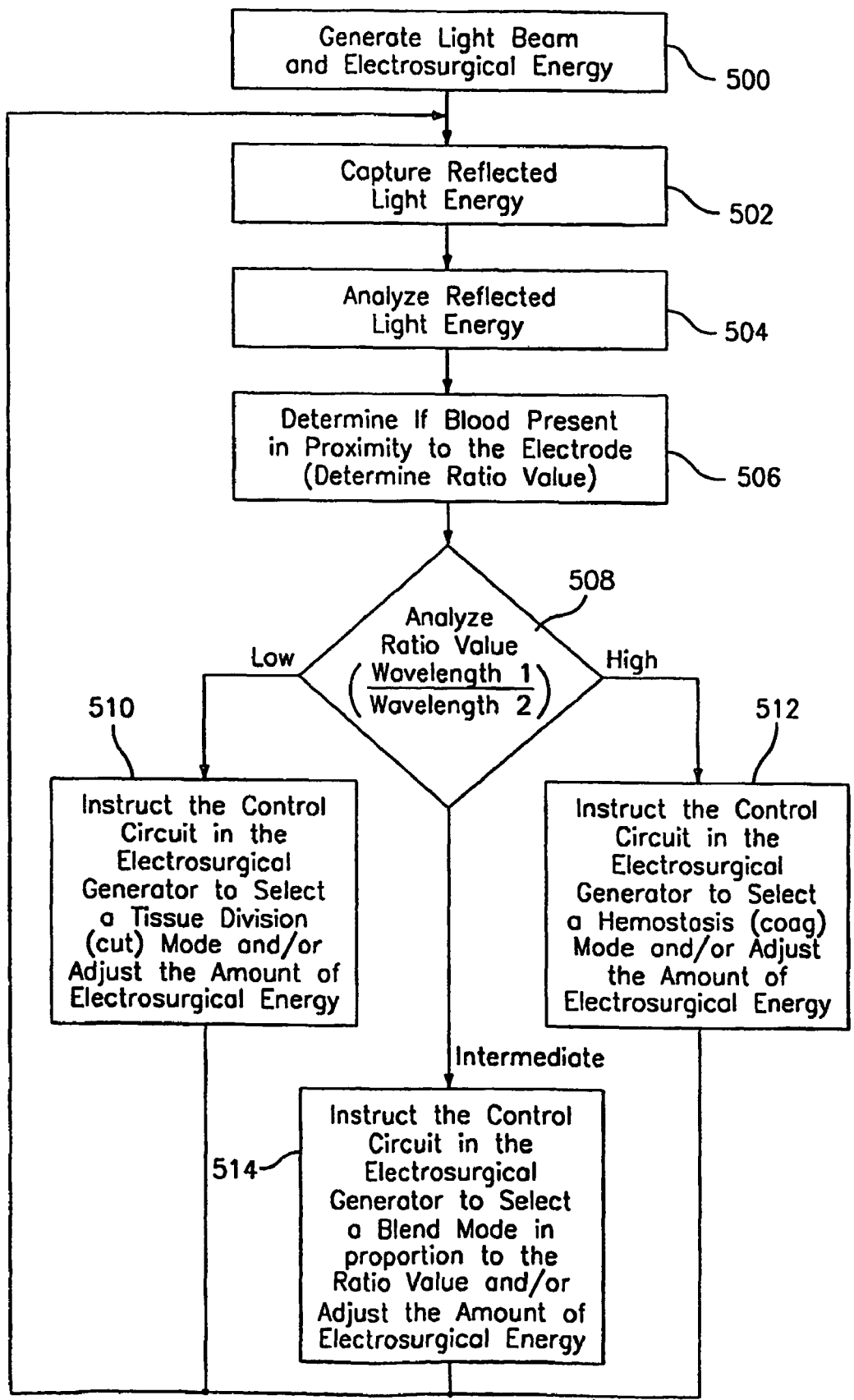
FIG. 5 is a flow chart showing the operation of the optical blood detection system according to a second method.

FIG. 5 is a flow chart illustrating another exemplary method of operation of the optical blood detection system 17. In step 500, the optical light beam and electrosurgical energy are generated. The reflected light energy is captured in step 502 and analyzed in step 504 to determine the amount of blood present in proximity to the electrode 16 at step 506. Step 506 determines the amount of blood present by calculating the ratio value as determined by dividing the photon counts at wavelength 1 by the photon counts at wavelength 2. The ratio value is analyzed at step 508.

If the ratio value is low (lower than a predetermined ratio value) then the process proceeds to step 510 where a signal is transmitted by the feedback correction circuit 58 to the electrosurgical generator 18 to control the mode of operation, namely, selecting a tissue division (cut) mode. Also, the amount of electrosurgical energy may be adjusted.

If at step 508, it is determined that the ratio value is high (greater than the predetermined ratio value), the process proceeds to step 512 where a signal is transmitted by the feedback correction circuit 58 to the electrosurgical generator 18 selecting a hemostasis (coagulation) mode. The amount of electrosurgical energy may also be adjusted.

If at step 508, it is determined that the ratio value is at an intermediate value (approximately equal to the predetermined ratio value), the process proceeds to step 514 where a signal is transmitted by the feedback correction circuit 58 to the electrosurgical generator 18 selecting a blended mode that is in proportion to the detected ratio value. Following either step 510, 512, or 514, the process returns to capture reflected light energy in step 502 in a continuous loop.

It is provided that depending on which of the above spectroscopy and other methods is used by the optical blood detection system 17 to determine the amount of blood present, the optical blood detection system 17 is controlled accordingly using known blood-related optical measurement parameters for each method, in order to generate and focus an optical light beam having characteristics suitable for the method. The optical blood detection system 17 can change the wavelength of the optical light beam within the visible, near-infrared and infrared light spectrum wavelengths depending on which of the above methods is being used for determining the amount of blood present in proximity to the electrode 16. For example, if the NIRS method is used, the optical light beam needs to have a wavelength just above the visible spectrum.

The wavelength of the optical light beam can be manually selected using a control knob or other control means on the optical blood detection system 17. If the wavelength of the optical light beam is in a particular range, the light energy of the optical light beam can be used to create an ionized conductive pathway along which the electrosurgical energy can be guided.

When the light energy is being used to create an ionized pathway, the light energy must be controlled using the control means in order to avoid undesired tissue effects. The duty cycle of the light beam should be kept in the range of $10^{-5}$ to $10^{-8}$. Energy density delivered to any single area of tissue from the light beam should not exceed 26 J/cm$^2$ for wavelengths between 1.06 and 10.6 microns, and 17 J/cm$^2$ for wavelengths around and below 0.53 microns. For creating the ionized pathway, the wavelength of the optical beam should be in the range of 0.3 to 10.6 microns.

It is further provided that one or more of the above-mentioned circuits 52, 56 and 58 can be implemented by one or more sets of programmable instructions configured for being executed by at least one processor of the electrosurgical system 10 or at least one processor remotely located from the electrosurgical system 10. For example, the data corresponding to the reflected light energy can be transmitted, either wirelessly or non-wirelessly, over a network, such as a LAN, WAN, or the Internet, to a remote server or control station for analyzing the data using a set of programmable instructions for determining the amount of blood present in proximity to and/or on the electrode 16 and/or the presence of blood vessels in proximity to the distal end of the electrode 16.

In accordance with the analysis performed, the remote server or control station then generates using the same or another set of programmable instructions the feedback control signal and supplies the signal to the power selection system. It is contemplated that another form of electromagnetic energy can be used to detect for the presence of blood besides the optical beam of light.

Figure 6:
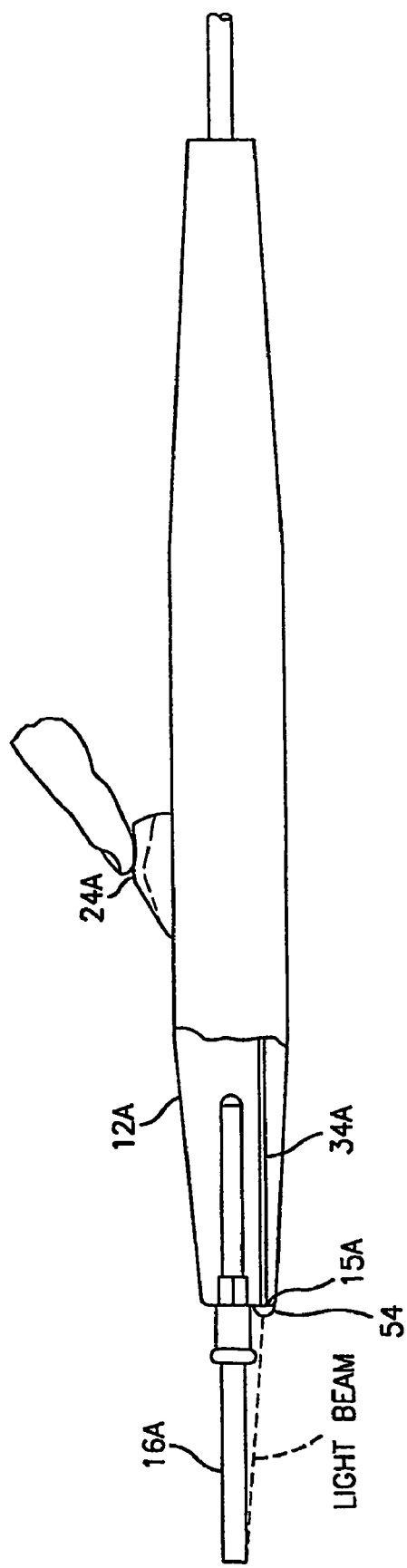
FIG. 6 is a cut-away, schematic diagram of another embodiment for the electrosurgical handpiece instrument.

Another embodiment for a handpiece for the electrosurgical system 10 is depicted by FIG. 6 and designated generally by reference numeral 12A. The handpiece 12A includes a proximal end 13A which is held and controlled by the surgeon. A distal end 14A on the handpiece 12A has a port 15A from which an optical light beam is directed to the patient 11. An electrosurgical electrode 16A extends from the distal end 14A of the handpiece 12A. The at least one optical component 54 at the distal end 14A of the handpiece 12A returns signals indicative of the reflected light energy to the optical blood detection system 17 via waveguide/wires 34 to at least one photosensitive detector.

A manually-actuated variable control button 24A is provided on the handpiece 12A for the real-time, selective control by the surgeon of the intensity or level of the current, i.e., intensity of the output waveform, provided by the electrosurgical generator 18 in accordance with the amount of blood detected by the optical blood detection system 17. Accordingly, the handpiece 12A provides the surgeon with the ability to control the amount of tissue cutting, coagulating, etc. as the system 10 concurrently detects the amount of blood.

In another preferred embodiment with continued reference to FIG. 6, the optical detection of the presence of blood controls the mode of the electrosurgical generator output in real-time or on-the-fly. For illustrative purposes, if a large amount of blood is detected adjacent to the electrode 16A then the electrosurgical generator output mode is automatically set for a high-level "hemostasis" (coag) waveform. If no blood is detected, then a "tissue division" (cut) waveform is automatically selected for the electrosurgical generator output. If an intermediate amount of blood is detected, then a "blend" is selected in proportion to the amount of blood detected. Simultaneously, the surgeon can use the manually-actuated variable control button 24A for real-time, selective control of the intensity or level of current.

The surgeon selects the intensity that provides an operational speed within his individual comfort zone. So the selection of the mode is automatically controlled by the blood detection circuit 56 and the surgeon controls the intensity of the output in real-time or on-the-fly. This embodiment greatly simplifies the surgeon-equipment interface by providing an automated mode select to assist the surgeon. As a result there is an improvement in the surgical outcome, because the appropriate mode is selected in real-time, thereby reducing thermal spread within the tissue. Additionally, since the surgeon maintains control of the intensity of the current, there is a built-in safety feature.

The above-described control scheme can be offered as a selectable feature or option. That is, a selectable switch would allow the surgeon to choose between operating the system of the present invention in a fully automatic mode or in a mode which enables the surgeon to control the intensity of the current.

It is contemplated that the control button 24A may also be located at the foot pedal 26. It is further contemplated that the functions of the variable control button 24A can be automated, in order for the system 10 to automatically control the intensity of the current in accordance with the amount of blood detected by the optical blood detection system 17.

It is provided that the surgeon can utilize the optical beam emanating from port 15A to pinpoint the target tissue to be treated if the optical light beam has light energy within the visible spectrum. It is envisioned that the optical light beam may have light energy within the visible, near-infrared and infrared light spectrum wavelengths.

Figure 2:
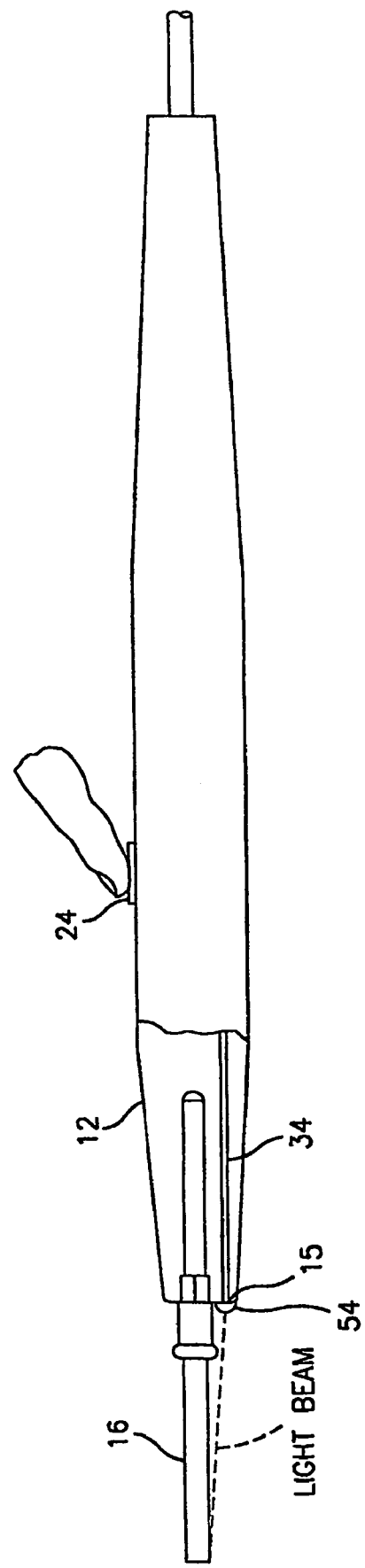
FIG. 2 is cut-away, schematic diagram of an electrosurgical handpiece instrument of the electrosurgical system of FIG. 1.

As shown by FIGS. 2 and 6, the electrosurgical system 10 is configured so the distal end 14, 14A and the electrosurgical electrode 16, 16A are preferably arranged geometrically relative to the handpiece 12, 12A to provide the light energy from the distal end 14, 14A. This geometry provides for the combined concurrent application of the light energy and the electrosurgical energy. The ionized pathway is formed by the light energy from the distal end 14, 14A to the patient 11 to direct the electrosurgical energy there along.

A method for providing cutting, coagulating, and/or a combination thereof on tissue of the patient 11 with the electrosurgical system 10 includes the following step of directing light energy and electrosurgical energy from the handpiece 12, 12A with its proximal and distal ends, 13, 13A and 14, 14A, along a longitudinal axis of the handpiece 12, 12A by aiming the distal end 14, 14A thereof along the longitudinal axis from which light energy and electrosurgical energy may be at least in part concurrently directed.

Preferably, as shown by FIGS. 2 and 6, the optical light beam is focused in front of the distal end 14, 14A of the electrode 16, 16A to detect blood present on tissue which is being cut or coagulated by the handpiece 12, 12A. The light energy is emanated continuously from the distal end 14, 14A of the handpiece 12, 12A. Or, alternatively, the surgeon activates the electrosurgical generator 18 using the control button 24, 24A on the handpiece 12, 12A or the footswitch 26. When activation is initiated, first, light energy is emitted from the distal end 14, 14A of the handpiece 12, 12A, then after a brief time delay in which the presence of blood is detected, the transmission of electrosurgical energy from the electrosurgical electrode 16, 16A at the distal end 14, 14A of the handpiece 12, 12A is enabled.

In the case of encountering a bleeding vessel that has created a pool of blood, this method provides detection of the pool of blood and automatic select of a hemostatic (coagulation) waveform by the electrosurgical generator 18 in order to affect a "spot coag" procedure.

Likewise, if no blood is present, the detection system selects a tissue division (cut) waveform. In this way, the thermal damage to the tissue is reduced creating a superior tissue effect.

The method includes the additional step of guiding the electrosurgical energy by arranging the distal end 14, 14A and the electrosurgical electrode 16, 16A geometrically relative to the handpiece 12, 12A for providing the optical light beam from the distal end 14, 14A for the combined concurrent application of the optical light beam and the electrosurgical energy. Then the added step of ionizing a conductive pathway with light energy from the distal end 14, 14A to the patient 11 to direct the flow of electrosurgical energy is performed.

The method also includes the additional step of providing an elongate electrosurgical electrode support for supporting the electrode 16, 16A for endoscopic or laparoscopic use where a cannula is placed through the patients body wall.

The claims which follow seek to cover the described embodiments and their equivalents. The concept in its broadest scope covers the system and methods for optically detecting the presence of blood and/or determining the amount of blood detected during electrosurgery. It is to be understood that the concept is subject to many modifications without departing from the spirit and scope of the claims as recited herein.

Although the subject invention has been described with respect to preferred embodiments, it will be readily apparent to those having ordinary skill in the art to which it appertains that changes and modifications may be made thereto without departing from the spirit or scope of the subject apparatus as defined by the appended claims.

The invention claimed is:

1. An electrosurgical system comprising:
   means for generating and directing broadband light energy of two different wavelengths onto tissue;
   means for generating electrosurgical energy and transmitting the same via an electrode to the tissue;
   means for capturing and analyzing characteristics of reflected broadband light energy and utilizing a ratio therebetween to determining an amount of blood present in proximity to the electrode and for controlling the means for generating electrosurgical energy accordingly; and
   means for selecting a first control mode when the ratio value is below the predetermined threshold value and a second control mode when the ratio value is above a predetermined threshold value.

2. The electrosurgical system of claim 1, wherein the means for generating and directing broadband light energy of two different wavelengths generates light energy in at least one of the visible, near-infrared and infrared light spectrum wavelengths.

3. The electrosurgical system of claim 1, wherein the means for generating electrosurgical energy generates electrosurgical energy having at least one of a tissue division and a coagulation output waveform.

4. The electrosurgical system of claim 1, wherein the reflected broadband light energy characteristics are selected from the group consisting of light intensity level, light scattering effects, and level of fluorescent energy.

5. The electrosurgical system of claim 1, wherein the means for capturing and analyzing is remotely located from the means for generating broadband light energy and the means for generating electrosurgical energy.

6. The electrosurgical system of claim 1, wherein the means for capturing and analyzing analyzes reflected broadband light energy characteristics using a technique selected from the group consisting of Near Infrared Spectroscopy, Infrared Spectroscopy, Fluorescence Spectroscopy, Raman Spectroscopy, Photoacoustic Spectroscopy, laser Doppler flowmetry, measurement of light scatter changes, and measurement of polarization changes.

7. The electrosurgical system of claim 1, wherein the broadband light energy has at least one wavelength suitable for creating an ionized pathway between a distal end of the electrode and the tissue, and the electrode is positioned near the ionized pathway such that the electrosurgical energy is conducted along the ionized pathway.

8. The electrosurgical system of claim 1, wherein the means for capturing and analyzing includes means for detecting the presence of at least one blood vessel in proximity to a distal end of the electrode.

9. The electrosurgical system of claim 1, wherein the means for capturing and analyzing reflected characteristics of the light energy includes means for determining the ratio value by dividing a first parameter obtained by directing light energy having a first wavelength from a second parameter obtained by directing light energy having a second wavelength.

10. The electrosurgical system of claim 9, wherein the means for capturing and analyzing reflected characteristics of the light energy further includes means for determining whether the ratio value is at least one of lower than, approximately equal to, and greater than a predetermined ratio value and for controlling the means for generating electrosurgical energy accordingly.

11. The electrosurgical system of claim 9, wherein the first wavelength is in the range of about 620 to about 700 nanometers and the second wavelength is in the range of about 950 to about 1050 nanometers.

12. The electrosurgical system of claim 1, wherein the means for controlling the source of electrosurgical energy includes means for variably controlling the intensity of the current generated by the electrosurgical generator.

13. A method for performing electrosurgery, the method comprising the steps of:
   supplying broadband light energy having at least two different wavelengths and electrosurgical energy to tissue via at least one instrument having a distal end;
   capturing and analyzing reflected characteristics of the broadband light energy utilizing a ratio value between the reflected characteristics of the two wavelengths to determine an amount of blood present in proximity to the at least one instrument and for controlling the delivery of electrosurgical energy accordingly;
   comparing the ratio value with a predetermined ratio value to control the amount of electrosurgical energy and to select at least one control mode of the source of electrosurgical energy accordingly; and
   selecting a first control mode when the ratio value is below a predetermined threshold and a second control mode when the ratio value is above a predetermined threshold.

14. The method of claim 13, wherein the step of capturing and analyzing reflected characteristics of the broadband light energy includes the step of using a technique selected from the group consisting of Near Infrared Spectroscopy, Infrared Spectroscopy, Fluorescence Spectroscopy, Raman Spectroscopy, Photoacoustic Spectroscopy, laser Doppler flowmetry, measurement of light scatter changes, and measurement of polarization changes.

15. The method of claim 13, further comprising the step of sequencing the delivery of broadband light energy and electrosurgical energy from the distal end for first creating an ionized pathway between the distal end and the tissue, and conducting electrosurgical energy along the ionized pathway.

16. The method of claim 13, wherein the analyzing step further includes the step determining the presence of at least one blood vessel in proximity to the at least one instrument.

17. The method of claim 13, wherein the step of capturing and analyzing reflected characteristics of the broadband light energy includes the step of determining the ratio value by dividing a first parameter obtained by supplying light energy having a first wavelength from a second parameter obtained by supplying light energy having a second wavelength.

18. The method of claim 17, wherein the step of capturing and analyzing reflected characteristics of the broadband light energy further includes the step of determining whether the ratio value is at least one of lower than, approximately equal to, and greater than a predetermined ratio value.

19. The method of claim 17, wherein the first wavelength is in the range of about 620 to about 700 nanometers and the second wavelength is in the range of about 950 to about 1050 nanometers.

20. The method of claim 13, wherein the step of capturing and analyzing reflected characteristics of the light energy includes the step of variably controlling the intensity of the current generated by the electrosurgical generator.

* * * * *